US006709650B1

(12) United States Patent
Sutton et al.

(10) Patent No.: US 6,709,650 B1
(45) Date of Patent: Mar. 23, 2004

(54) SPRAY-DRIED MICROPARTICLES AND THEIR USE AS THERAPEUTIC VEHICLES

(75) Inventors: Andrew D. Sutton, Ruddington (GB); Richard A. Johnson, West Bridgford (GB); Peter J. Senior, Near Melbourne (GB); David Heath, The Park (GB)

(73) Assignee: Elam Drug Delivery Limited, Nottingham (GB)

( * ) Notice: Subject to any disclaimer, the term of this patent is extended or adjusted under 35 U.S.C. 154(b) by 0 days.

(21) Appl. No.: 09/382,561

(22) Filed: Aug. 25, 1999

Related U.S. Application Data

(63) Continuation of application No. 08/487,420, filed on Jun. 7, 1995, now Pat. No. 5,993,805, which is a continuation-in-part of application No. 07/956,875, filed as application No. PCT/GB92/00643 on Apr. 10, 1992, now Pat. No. 5,518,709.

(30) Foreign Application Priority Data

Apr. 10, 1991 (GB) ............................................. 9107628
Sep. 29, 1994 (EP) ............................................. 94307126

(51) Int. Cl.[7] .......................... A61K 38/43; A61K 9/14; A61K 9/50
(52) U.S. Cl. ........................ 424/94.1; 424/9.5; 424/9.6; 424/46; 424/94.3; 424/94.4; 424/491; 424/499; 514/965
(58) Field of Search ..................... 428/402.24; 424/9.5, 424/9.52, 2.6, 46, 94.1, 94.3, 434, 484, 491, 493, 498, 499, 9.6; 128/203.15; 514/965

(56) References Cited

U.S. PATENT DOCUMENTS

| | | |
|---|---|---|
| 2,739,167 A | 3/1956 | Conn |
| 2,797,201 A | 6/1957 | Veatch et al. |
| 3,501,419 A | 3/1970 | Bridgeford et al. |
| 3,664,963 A | 5/1972 | Pasin ........................ 264/4 X |
| 3,809,294 A | 5/1974 | Torgeson .................... 222/182 |
| 3,937,668 A | 2/1976 | Zolle |
| 4,089,800 A | 5/1978 | Temple ....................... 264/4.6 |
| 4,093,709 A | 6/1978 | Choi et al. |
| 4,107,288 A | 8/1978 | Oppenheim et al. ..... 428/402.2 |
| 4,127,622 A | 11/1978 | Watanabe et al. ............. 264/13 |
| 4,131,648 A | 12/1978 | Choi et al. |
| 4,138,344 A | 2/1979 | Choi et al. ....................... 252/1 |
| 4,147,767 A | 4/1979 | Yapel et al. |
| 4,180,646 A | 12/1979 | Choi et al. .................. 528/153 |
| 4,247,406 A | 1/1981 | Widder et al. ........... 252/62.53 |
| 4,276,885 A | 7/1981 | Tickner et al. .............. 128/660 |
| 4,316,341 A | 2/1982 | Landry .................... 73/861.25 |
| 4,349,530 A | 9/1982 | Royer |
| 4,357,259 A | 11/1982 | Senyei et al. |
| 4,420,442 A | 12/1983 | Sands .......................... 364/13 |
| 4,442,843 A | 4/1984 | Rasor et al. ................ 128/660 |
| 4,466,442 A | 8/1984 | Hillmann et al. ........... 128/653 |
| 4,572,203 A | 2/1986 | Feinstein .................... 128/661 |
| 4,649,911 A | 3/1987 | Knight et al. .......... 128/200.21 |
| 4,671,954 A | 6/1987 | Goldberg et al. ............ 424/450 |
| 4,675,381 A | 6/1987 | Bichon ........................ 530/345 |
| 4,774,958 A | 10/1988 | Feinstein ............... 128/660.01 |
| 4,808,408 A | 2/1989 | Baker et al. ................. 424/408 |
| 4,832,941 A | 5/1989 | Berwing et al. |
| 4,844,882 A | 7/1989 | Widder et al. .................. 424/9 |
| 4,888,398 A | 12/1989 | Bichon et al. .............. 525/420 |
| 4,892,733 A | 1/1990 | Bichon et al. .............. 424/422 |
| 4,900,540 A | 2/1990 | Ryan et al. ...................... 424/9 |
| 4,957,656 A | 9/1990 | Cerny et al. |
| 4,960,351 A | 10/1990 | Kendall, Jr. et al. ............. 425/6 |
| 4,968,562 A | 11/1990 | Delgado ..................... 428/402 |
| 4,981,625 A | 1/1991 | Rhim et al. .................... 264/13 |
| 5,089,181 A | 2/1992 | Hauser ........................ 264/4.3 |
| 5,137,928 A | 8/1992 | Erbel et al. .................... 521/56 |
| 5,190,982 A | 3/1993 | Erbel et al. .................... 521/56 |
| 5,196,183 A | 3/1993 | Yudelson et al. ............... 424/9 |
| 5,205,287 A | 4/1993 | Erbel et al. ................. 128/632 |
| 5,380,519 A | 1/1995 | Schneider et al. ............. 424/9 |
| 5,425,366 A | 6/1995 | Reinhardt et al. ...... 128/662.02 |
| 5,501,863 A | 3/1996 | Rossling et al. ............ 424/489 |
| 5,518,709 A | 5/1996 | Sutton et al. ............... 424/9.52 |
| 5,993,805 A * | 11/1999 | Sutton et al. .............. 424/94.1 |
| 6,022,525 A * | 2/2000 | Sutton et al. .............. 424/9.52 |
| 6,264,959 B1 * | 7/2001 | Stein et al. .............. 424/9.5 X |
| 6,509,006 B1 * | 1/2003 | Platz et al. .................... 424/46 |

FOREIGN PATENT DOCUMENTS

| | | |
|---|---|---|
| AU | A-80297/91 | 1/1992 |
| CA | 2 036 107 | 8/1991 |
| EP | 052 575 | 5/1982 |
| EP | 091 555 | 10/1983 |
| EP | 130 935 | 1/1985 |
| EP | 131 540 | 1/1985 |
| EP | 201 239 | 11/1986 |
| EP | 202 017 | 11/1986 |
| EP | 224 934 | 10/1987 |
| EP | 286 424 | 10/1988 |
| EP | 327 490 | 2/1989 |
| EP | 322 094 | 6/1989 |
| EP | 324 938 | 7/1989 |
| EP | 381 543 | 8/1990 |
| EP | 0 383 569 | 8/1990 |
| EP | 458 079 | 4/1991 |
| EP | 458 745 | 4/1991 |
| EP | 494 615 | 4/1992 |
| EP | 0 520 748 | 12/1992 |

(List continued on next page.)

OTHER PUBLICATIONS

Aldrich et al. (1974) "Use of the spinning disk technique to produce monodisperse microspheres of Human Serum Albumin for labeling with radioisotopes" *Int J Appl Rad and Isot* 25:15–18.

(List continued on next page.)

*Primary Examiner*—Richard D. Lovering
(74) *Attorney, Agent, or Firm*—Morrison & Foerster LLP

(57) ABSTRACT

Microparticles of a water-soluble material, which are smooth and spherical, and at least 90% of which have a mass median particle size of 1 to 10 $\mu$m, and which carry a therapeutic or diagnostic agent can successfully be used in dry powder inhalers to deliver the said agent.

20 Claims, 4 Drawing Sheets

FOREIGN PATENT DOCUMENTS

| | | |
|---|---|---|
| EP | 0 554 213 A1 | 8/1993 |
| EP | 606 486 A1 | 7/1994 |
| EP | 611 567 A1 | 8/1994 |
| GB | 1 288 583 | 9/1972 |
| JP | 56-129035 | 10/1981 |
| JP | 04-145131 | 5/1992 |
| NZ | 227869 | 2/1989 |
| WO | WO 84/02838 | 8/1984 |
| WO | WO 87/03891 | 7/1987 |
| WO | WO 90/13730 | 11/1990 |
| WO | WO 91/01706 | 2/1991 |
| WO | WO 91/06286 | 5/1991 |
| WO | WO 91/09629 | 7/1991 |
| WO | WO 91/12823 | 9/1991 |
| WO | WO 91/15244 | 10/1991 |
| WO | WO 91/16080 | 10/1991 |
| WO | WO 91/16882 | 11/1991 |
| WO | WO 92/05806 | 4/1992 |
| WO | WO 92/17212 | 10/1992 |
| WO | WO 92/17213 | 10/1992 |
| WO | WO 92/18164 | 10/1992 |
| WO | WO 93/02712 | 2/1993 |
| WO | WO 93/17713 | 9/1993 |
| WO | WO 94/08627 | 4/1994 |
| ZA | 890873 | 2/1989 |

OTHER PUBLICATIONS

Allcock (1976) "Polyphosphazenes: New Polymers with Inorganic Backbone Atoms" *Science* 193:1214–1219.

Angeloni et al. (1982) "The Mannich Bases in Polymer Synthesis: 3.* Reduction of Poly(β–Aminoketone)s to Poly(γ–Aminoalcohol)s and Their N–Alkylation to Poly(γ–Hydroxyquaternary Ammonium Salt)s" *Polymer* 23:1693–1697.

Barnhart et al. (1990) "Characteristics of Albunex. AirFilled Albumin Microspheres for Echocardiography Contrast Enhancement" *Invest. Radiol.* 25:S162–S164.

Baveja et al. (1986) "Microencapsulation of soluble pharmaceuticals" *J. Microencapsulation* 3:33–37.

Beller et al. (1979) "Assessment of Regional Myocardial Perfusion by Positron Emission Tomography after Intracoronary Administration of Gallium–68 Labeled Albumin Microspheres" *J. Comput. Assist. Tomogr.* 3:447–452.

Buchanan et al. (1969) "Labeling Albumin Microspheres with $^{113m}$In" *J. Nucl. Med.* 10:487–490.

Cheng et al. (1987) "The Production and Evaluation of Contrast–Carrying Liposomes Made with an Automatic High–Pressure System" *Invest. Radiol.* 22:47–55.

Clausen et al. (1981) "Distribution of blood flow in the dog kidney. III. Local update of 10 μm and 15 μm microspheres during renal vasodilation and constriction" *Acta Physiol. Scand.* 113:471–479.

Conte et al. (1994) "Spray Dried Albumin Microspheres Containing Nicardipine", *European J. Pharmaceutics and Biopharmaceutics* 40:203–208.

Cremers et al. (1990) "Albumin–Heparin Microspheres as Carriers for Cytostatic Agents" *J. Controlled Release* 11:167–179.

Deasy (1984) "Coacervation–Phase Separation Procedures Using Aqueous Vehicles" *Microencapsulation and Related Drug Processes*, New York: Marcel Dekker, Inc., pp. 61–69.

Durand–Keklikian et al. (1988) "Microencapsulation of Oil Droplets by Aerosol Techniques—I. Metal Oxide Coatings" *J. Aersol Sci.* 19:511–521.

Ellison (1967) "Adaptation of the Spinning Top Generator to Provide Aerosols in the Respirable Range" *Ann. Occup. Hyg.* 10:363–367.

English Language Translation of Japanese Patent No. 56–129035.

English Language Abstract of Japanese Patent No. 04–145131 Patent Abstracts of Japan (JPO and Japio, 1992).

Feinstein et al. (1984) "Microbubble Dynamics Visualized in the Intact Capillary Circulation" *JACC* 4:595–600.

Galyean et al. (1979) "Chromatography and Electrophoresis of Native and Spray–Dryed Egg White" *J. Food Science* 44:1345–1349.

Gramiak et al. (1969) "Ultrasound Cardiography: Contrast Studies in Anatomy and Function" *Radiology* 92:939–948.

Grinstaff et al. (1991) "Air–Filled Proteinaceous Microbubbles: Synthesis of an Echo–Contrast Agent" *Proc. Natl. Acad. Sci. USA* 88:7708–7710.

Gupta et al. (1989) "Albumin Microspheres I:Physico-Chemical Characteristics" *J. Microencap.* 6:427–462.

Haghpanah et al. (1994) British Pharmaceutical Conference, King's College, London.

Heller (1980) "Controlled Release of Biologically Active Compounds From Bioerodible Polymers" *Biomaterials* 1:51–57.

Kawashima et al. (1991) "Preparation of Multiple Unit Hollow Microspheres (Microballoons) With Acrylic Resin Containing Tranilast and Their Drug Release Characteristics (in Vitro) and Floating Behavior (in Vitro)" *J. Controlled Release* 16:297–290.

Kondo (1980) "Microcapsule Processing and Technology" Van Valkenburg, J.W. (Ed.), New York: Marcel Dekker, Inc., pp. 18–20, 61, 68, 70, 90–92, 106–109, 118–119.

Kramer (1974) "Albumin Microspheres as Vehicles for Achieving Specificity in Drug Delivery" *J. Pharmaceutical Science* 63:1646–1647.

Kwok et al. (1991) "Production of 5–51 μm Diameter Alginate–Polylysine Microcapsules by an Air–Atomization Technique" *Pharm. Res.* 8:341–344.

Levy et al. (1991) "Mixed–walled microcapsules made of cross–linked proteins and polysaccharides: preparation and properties" *J. Microencapsulation* 8:335–347.

McArdle et al. (1988) "Cytoxic–loaded albumin microspheres: a novel approach to regional chemotherapy" *Br. J. Surg.* 75:132–134.

Modler et al. (1978) "Calcium as an Adjuvant for Spray–Drying Acid Whey" *J. Dairy Sci.* 61:294–299.

Morris et al. (1982) "Three–ply walled w/o/w microcapsules formed by a multiple emulsion technique" *J. Pharm. Pharmacol.* 34:475–479.

Morris et al. (1984) "Particle size analysis of microcapsules" *J. Pharm. Pharmacol.* 36:73–76.

Omotosho et al. (1986) "The nature of the oil phase and the release of solutes from multiple (w/o/w) emulsions" *J. Pharm. Pharmacol.* 38:865–870.

Ophir et al. (1979) "Aqueous Solutions as Potential Ultrasonic Contrast Agents" *Ultrasonic Imaging* 1:265–279.

Ophir et al. (1980) "Ultrasonic Backscatter From Contrast Producing Collagen Microspheres" *Ultrasonic Imaging* 2:67–77.

Pande et al. (1990) "Preparation, characterization and performance evaluation of neomycin–HSA microspheres" *J. Microencapsulation* 7:155–165.

Parkinson (1975) "Effects of Spray–Drying and Freezing on the Proteins of Liquid Whole Egg" *J. Sci. Fd. Agric.* 26:1625–1637.

Porter et al. (1992) "The polyoxyethylene/polyoxypropylene block co–polymer Poloxamer–407 selectively redirects intravenously injected microspheres to sinusoidal endothelial cells of rabbit bone marrow" *FEBS Lett.* 305:62–66.

Przyborowski et al. (1982) "Preparation of HSA Microsphere in a One–Step Thermal Denaturation of Protein Aerosol Carried in Gas Medium" *E. J. Nucl. Med.* 7:71–72.

Raju et al. (1978) "Human Serum Albumin Microspheres for Lung Imaging–Preparation and Evaluation" *Isotopenpraxis* 14:57–61.

Rettenmaier et al. (1985) "In Vivo Alteration of Res Phagocytosis by Magnetic Albumin Microsphere" *J. Clin. Lab. Immunol.* 17:99–103.

Rosenberg et al. (1990) "Factors Affecting Retention in Spray–Drying Microencapsulation of Volatile Materials" *J. Agric. Food Chem.* 38:1288–1294.

Sato et al. (1988) "Porous Biodegradable Microspheres for Controlled Drug Delivery, I. Assessment of Processing Conditions and Solvent Removal Techniques" *Pharm. Res.* 5:21–30.

Scheffel et al. (1972) "Albumin Microspheres for Study of the Reticuloendothelial System" *J. Nucl. Med.* 13:498–503.

Schlief (1991) "Ultrasound contrast agents" *Curr. Opin. Radiol.* 3:198–207.

Schneider et al. (1992) "Polymeric Microballoons as Ultrasound Contrast Agents Physical and Ultrasonic Properties Compared with Sonicated Albumin" *Invest. Radiol.* 27:134–139.

Schroderer et al. (1977) "Distribution of Radiolabeled Subvisible Microspheres After Intravenous Adminstration of Beagle Dogs" *J. Pharmaceutical Science* 67:504–507.

Shah et al. (1987) "An evaluation of albumin microcapsules prepared using a multiple emulsion technique" *J. Microencapsulation* 4:223–238.

Shapiro et al. (1990) "Intravenous Contrast Echocardiography With Use of Sonicated Albumin in Humans; Systolic Disappearance of Left Ventricular Contrast After Transpulmonary Transmission" *JACC* 16:1603–1607.

Takenaka et al. (1980) "Preparation of Enteric–Coated Microcapsules for Tableting by Spray–Drying Technique and In Vitro Simulation of Drug Release from the Tablet in GI Tract" *J. Pharm. Sci.* 69:1388–1392.

Takenaka et al. (1982) "Mechanical Properties, Dissolution Behavior and Stability to Oxidation of $_L$–Ascorbylmonostearate Microcapsule Prepared by a Spray–Drying Polycondensation Technique" *Chem. Pharm. Bull.* 30:2189–2195.

Violante et al. (1981) "Biodistribution of a Particulate Hepatolienographic CT Contrast Agent: A Study of Iodipamide Ethyl Ester in the Rat" *Invest. Radiol.* 16:40–45.

Wheatley et al. (1990) "Contrast Agents for Diagnostic Ultrasound: Development and Evaluation of PolymerCoated Microbubbles" *Biomaterials* 11:713–717.

White et al. (1990) "Biodistribution and Clearance of Contrast–Carrying MREV Liposomes" *Invest. Radiol.* 25:1125–1129.

Widder et al. (1979) "Magnetically Responsive Microspheres and Other Carriers for the Biophysical Targeting of Antitumor Agents" *Advances in Pharmacology and Chemotherapy* 16:213–269.

Wilkins et al. (1966) "Studies on the Relationship Between the Electrophoretic Properties of Colioids and Their Blood Clearance and Organ Distribution in the Rat" *Br. J. Exp. Pathol.* 47:568–576.

Zhang et al. (1991) "Histochemical studies on the mechanism of macromolecule leakage across the glomerular capillary wall" *Histochem.* 96:115–121.

Ancesehi et al. (1990) "Immunochemical and Immunohistochemical evaluation of lung permeability in ventilated newborn rabbits" *Experimental Lung Research* 16:593–605.

Berthiaume et al. (1989) "Protein clearance from the air spaces and lungs of unanesthetized sheep over 144 h" *J. Appl. Physiol.* 67:1887–1897.

Clay et al. (1983) "Factors influencing the size distribution of aerosols from jet nebulisers" *Thorax* 38:755–759.

Csernus et al. (1990) "Release of peptides from sustained delivery systems (microcapsules and microparticles) in vivo" *Int. J. Peptide Protein Res.* 35:557–565.

Folkesson et al. (1993) "Lung to blood passage of albumin and a nonapeptide after intratracheal instillation in the young developing pig" *Acta Physiologica Scandinavica* 147:173–178.

Gupta et al. (1991) "Contemporary approaches in aerosolized drug delivery to the lung" *Journal of Controlled Release* 17:129–148.

Hermens (1992) "Delivery of hormones: some new concepts" *Pharmaceutisch Weekblad Scientific edition* 14:253–257.

Kim et al. (1985) "Asymmetric [$^{14}$C] albumin transport across bullfrog alveolar epithelium" *J. Appl. Physiol.* 59:1290–1297.

Masinde et al. (1993) "Aerosolized aqueous suspensions of poly($_L$ –lactic acid) microspheres" *International Journal of Pharmaceutics* 100:123–131.

Matthys et al. (1985) "Pulmonary deposition of aerosols by different mechanical devices" *Respiration* 48:269–276.

Maulding "Prolonged delivery of peptides by microcapsules" 167–176.

Morén (1985) "Aerosol dosage forms and formulations" *Aerosols in Medicine. Principles, Diagnosis and Therapy* Moren et al (Eds.) Elsevier Science Publishers 261–287.

McMartin et al. (1987) "Analysis of structural requirements for the absorption of drugs and macromolecules from the nasal cavity" *Journal of Pharmaceutical Sciences* 76:535–540.

Pauwels (1985) "Pharmacokinetics of inhaled drugs" *Aerosols in Medicine, Principles, Diagnosis and Therapy* Moren et al. (Eds.) Elsevier Science Publishers 219–224.

Pontiroli et al. (1989) "Intranasal drug delivery potential advantages and limitations from a clinical pharmacokinetic perspective" *Clin. Pharmacokinet* 17:299–307.

Pontiroli et al. (1990) "Intranasal administration of peptide hormones: factors affecting transmucosal absorption" *Diabetic Medicine* 7:770–774.

Ting et al. (1992) "Microparticles of polyvinyl alcohol for nasal delivery. I. Generation by spray–drying and spay–desolvation" *Pharmaceutical Research* 9:1330–1335.

Valeyre et al. (1991) "Glucose, K$^+$, and albumin concentrations in the alveolar milieu of normal humans and pulmonary sarcoidosis patients" *AM Rev Respir Dis* 143:1096–1101.

Wall et al. (1994) "Administration as hydroxypropyl β–cyclodextrin complexes does not slow rates of pulmonary drug absorption in rat" *S.T.P. Pharma Sciences* 4(1):63–68.

Maulding, H. V. (1987). "Prolonged Delivery of Peptides by Microcapsules" In*Advances in Drug Delivery Systems, 3, Third International Symposium, Salt Lake City, UT, USA, Feb. 24–27, 1987*, Anderson,J.M. and Kim, S.W., eds. Elsevier Science Publishers: Amsterdam. pp. 167–176.

* cited by examiner

SPRAY-DRIED MICROPARTICLES AND THEIR USE AS THERAPEUTIC VEHICLES

REFERENCE TO EARLIER APPLICATION

This Application is a continuation of application Ser. No. 08/487,420 filed Jun. 7, 1995, now U.S. Pat. No. 5,993,805, which is a continuation-in-part of application Ser. No. 07/956,875 filed Mar. 15, 1993, now U.S. Pat. No. 5,518,709, which is a 371 of PCT/GB99/00643 filed Apr. 10, 1992.

FIELD OF THE INVENTION

This invention relates to spray-dried microparticles and their use as therapeutic vehicles. In particular, the invention relates to means for delivery of diagnostic and therapeutic agents and biotechnology products, including therapeutics based upon rDNA technology.

BACKGROUND OF THE INVENTION

The most commonly used route of administration of therapeutic agents, oral or gastrointestinal, is largely inapplicable to peptides and proteins derived from the rDNA industry. The susceptibility of normally blood-borne peptides and proteins to the acidic/proteolytic environment of the gut, largely precludes this route for administration. The logical means of administration is intravenous, but this presents problems of poor patient compliance during chronic administration and very often rapid first-pass clearance by the liver, resulting in short IV lifetimes.

Recently, the potential for delivery by mucosal transfer has been explored. Whilst nasal delivery has been extensively explored, the potential delivery of peptides via the pulmonary airways is largely unexplored.

Alveolar cells, in their own right, provide an effective barrier. However, even passage of material to the alveolar region represents a significant impediment to this method of administration. There is an optimal size of particle which will access the lowest regions of the pulmonary airways, i.e. an aerodynamic diameter of <5 μm. Particles above this size will be caught by impaction in the upper airways, such that in standard commercial suspension preparations, only 10–30% of particles, from what are normally polydispersed suspensions, reach the lowest airways.

Current methods of aerosolising drugs for inhalation include nebulisation, metered dose inhalers and dry powder systems. Nebulisation of aqueous solutions requires large volumes of drugs and involves the use of bulky and non-portable devices.

The most common method of administration to the lung is by the use of volatile propellant-based devices, commonly termed metered dose inhalers. The basic design is a solution of propellant, commonly CFC 11, 12 or 114, containing either dissolved drug or a suspension of the drug in a pressurised canister. Dosing is achieved by depressing an actuator which releases a propellant aerosol of drug suspension or solution which is carried on the airways. During its passage to the lung, the propellant evaporates to yield microscopic precipitates from solution or free particles from suspension. The dosing is fairly reproducible and cheap but there is growing environmental pressure to reduce the use of CFCs. Furthermore, the use of CFC solvents remains largely incompatible with many of the modern biotechnology drugs, because of their susceptibility to denaturation and low stability.

Concurrently, there is a move toward dry powder devices which consist of dry powders of drugs usually admixed with an excipient, such as lactose or glucose, which facilitates the aerosolisation and dispersion of the drug particles. The energy for disaggregation is often supplied by the breath or inspiration of air through the device.

Drugs are currently micronised, to reduce particle size. This approach is not applicable for biotechnology products. In general, biotechnology products are available in low quantity and, furthermore, are susceptible to the methods currently employed to dry and micronise prior to mixing with excipient. Further, it is particularly difficult to provide blends of drug and excipient which are sufficiently free-flowing that they flow and dose reproducibly in the modern multiple dose inhalers such as the Turbohaler (Astra) and Diskhaler (Glaxo). Studies have revealed that, contrary to expectation, spray-dried (spherical) salbutamol microparticles showed greater forces of cohesion and adhesion than similarly-sized particles of micronised drug. Electron micrographs of the spray-dried material revealed the particles to possess pitted, rough surfaces.

Haghpanah et al reported, at the 1994 British Pharmaceutical Conference, that albumin microparticles incorporating salbutamol, had been produced by spray-drying and were of a suitable size for respiratory drug delivery, i.e. 1–5 μm. The aim was to encapsulate salbutamol, for slow release. It does not appear that the product is of substantially uniformly spherical or smooth microparticles that have satisfactory flow properties, for multi-dose dry powder inhalers.

Diagnostic agents comprising hollow microcapsules have been used to enhance ultrasound imaging. For example, EP-A-458745 (Sintetica) discloses a process of preparing air- or gas-filled microballoons by interfacial polymerisation of synthetic polymers such as polylactides and polyglycolides. WO-A-91/12823 (Delta) discloses a similar process using albumin. Wheatley et al (1990) Biomaterials 11:713–717, disclose ionotropic gelation of alginate to form microbubbles of over 30 μm diameter. WO-A-91/09629 discloses liposomes for use as ultrasound contrast agents.

Przyborowski et al, Eur. J. Nucl. Med. 7:71–72 (1982), disclose the preparation of human serum albumin (HSA) microspheres by spray-drying, for radiolabelling, and their subsequent use in scintigraphic imaging of the lung. The microspheres were not said to be hollow and, in our repetition of the work, predominantly poorly formed solid microspheres are produced. Unless the particles are hollow, they are unsuitable for echocardiography. Furthermore, the microspheres were prepared in a one-step process which we have found to be unsuitable for preparing microcapsules suitable for echocardiography; it was necessary in the prior process to remove undenatured albumin from the microspheres, and a wide size range of microspheres was apparently obtained, as a further sieving step was necessary.

Przyborowski et al refer to two earlier disclosures of methods of obtaining albumin particles for lung scintigraphy. Aldrich & Johnston (1974) Int. J. Appl. Rad. Isot. 25:15–18, disclose the use of a spinning disc to generate 3–70 μm diameter particles which are then denatured in hot oil. The oil is removed and the particles labelled with radioisotopes. Raju et al (1978) Isotopenpraxis 14(2):57–61, used the same spinning disc technique but denatured the albumin by simply heating the particles. In neither case were hollow microcapsules mentioned, and the particles prepared were not suitable for echocardiography.

EP-A-0606486 (Teijin) describes the production of powders in which an active agent is incorporated into small particles, with carriers comprised of cellulose or cellulose derivatives. The intention is to prevent drug particles from adhering to the gelatin capsules used in a unit dose dry powder inhaler. Page 12 of this publication refers to the spray-drying of "medicament and base", to obtain particles of which 80% or more were 0.5–10 µm in size. No directions are given as to what conditions should be used, in order to obtain such a product.

EP-A-0611567 (Teijin) is more specifically concerned with the production of powders for inhalation, by spray-drying. The carrier is a cellulose, chosen for its resistance to humidity. The conditions that are given in Example 1 (ethanol as solvent, 2–5% w/v solute) mean that there is no control of surface morphology, and Example 4 reports a poor lower airway respirable fraction (12%), indicating poor dispersion properties. Spherical particles are apparently obtained at high drug content, indicating that particle morphology is governed by the respective drug and carrier contents.

Conte et al (1994) Eur. J. Pharm. Biopharm. 40(4):203–208, disclose spray-drying from aqueous solution, with a maximum solute concentration of 1.5%. High drug content is required, in order to obtain the most nearly spherical particles. This entails shrunken and wrinkled particle morphology. Further, after suspension in butanol, to facilitate Coulter analysis, sonication is apparently necessary, implying that the particles are not fully dry.

It is an object behind the present invention to provide a therapeutic delivery vehicle and a composition that are better adapted than products of the prior art, for delivery to the alveoli in particular.

SUMMARY OF THE INVENTION

According to the present invention, it has surprisingly been found that, in microparticles (and also microcapsules and microspheres) that are also suitable as an intermediate product, i.e. before fixing, in the production of air-containing microcapsules for diagnostic imaging, the wall-forming material is substantially unaffected by spray-drying. Thus, highly uniform microparticles, microspheres or microcapsules of heat-sensitive materials such as enzymes, peptides and proteins, e.g. HSA, and other polymers, may be prepared and formulated as dry powders.

By contrast to the prior art, it has now been found that effective, soluble carriers for therapeutic and diagnostic agents can be prepared, by spray-drying, and which are free-flowing, smooth, spherical microparticles of water-soluble material, e.g. human serum albumin (HSA), having a mass median particle size of 1 to 10 µm. More generally, a process for preparing microcapsules of the invention comprises atomising a solution (or dispersion) of a wall-forming material. A therapeutic or diagnostic agent may be atomised therewith, or coupled to the microcapsules thus produced. Alternatively, the material may be an active agent itself. In particular, it has been found that, under the conditions stated herein, and more generally described by Sutton et al (1992), e.g. using an appropriate combination of higher solute concentrations and higher air:liquid flow ratios than Haghpanah et al, and shell-forming enhancers, remarkably smooth spherical microparticles of various materials may be produced. The spherical nature of the microparticles can be established by means other than mere maximum size analysis, i.e. the laser light diffraction technique described by Haghpanah et al. Moreover, the particle size and size distribution of the product can be controlled within a tighter range, and with greater reproducibility. For example, by Coulter analysis, 98% of the particles can be smaller than 6 µm on a number basis, within an interquartile range of 2 µm, and with less than 0.5 µm mean size variation between batches. Furthermore, when tested in a dry powder inhaler under development, reproducible dosing was achieved, and subsequent aerosolisation under normal flow conditions (30 l/min) resulted in excellent separation of microparticles from excipient.

Unfixed capsules of this invention, composed of non-denatured HSA or other spray-dryable material, possess highly smooth surfaces and may be processed with relatively low levels of excipients to produce free-flowing powders ideal for dry powder inhalers. Using this approach, it is possible to produce heterogeneous microcapsules which are comprised of a suspending polymer and active principle. This has the advantage of yielding free-flowing powder of active principles which may be further processed to give powders that dose and aerosolise with excellent reproducibility and accuracy.

In addition, the process of spray-drying, in its current form, gives rise to relatively little denaturation and conversion to polymers in the production of the free-flowing powder. In all cases, the size of the microcapsule suspension can be such that 90% of the mass lies within the desired size, e.g. the respirable region of 1–5 µm.

In essence therefore we have defined how to produce microparticles which are: predominantly 1–5 µm in size; smooth and spherical; gas-containing; and composed of undamaged protein molecules and which may be stored and shipped prior to other processing steps. In preparing intermediate microcapsules for ultrasound imaging, we have defined those characteristics of a process and the resulting powder which are essential for the production of superior powders for dry powder inhalers (DPI's). We find that many of the assays which have been developed for the echocontrast agent are suitable for defining those parameters of the particles which are advantageous for DPI powders, namely; echogenicity and pressure resistance of cross-linked particles defining perfectly formed microparticles; microscopic evaluation in DPX or solvents, defining sphericity and gas-containing properties of soluble intermediate capsules; size and size distribution analysis and also the monomeric protein assay to define the final level of fixation of the product.

Especially for use in therapy, considerable care is necessary in order to control particle size and size distribution. We have chosen a biocompatible polymer which when cross-linked remains innocuous and also learned how to reproducibly cross-link this molecule. In order to achieve controlled cross-linking, we have divorced the processes of microparticle formation and cross-linking which other emulsion and solvent evaporation process do not. This means that the initial step of the process does not damage the wall-forming material. We have defined the particular parameters which are important for complete particle formation and further defined more advantageous conditions which yield more intact particles. In choosing HSA as a particularly favourable polymer we have also chosen a potential carrier molecule which may: protect labile molecules; enhance uptake of peptides across the lung; bind low molecular weight drug through natural binding affinities; and be covalently modified to carry drugs across cellular barriers to the systemic circulation and beyond.

When researchers have used spray-drying to produce microparticles of small dimensions, they have tended to use volatile solvents, which encourages rapid droplet shrinkage. Alternatively, researchers have used feedstocks with low solute content in order to keep the solution viscosity low, to enhance smaller droplet production. In both cases, when the microparticles are produced, the process has little impact on the final morphology; rather this is dictated by the components used to form the particles. We have taken the extensive learning of how to produce controlled sized particles from HSA and applied this to many other materials including active drugs. We are able to use relatively high solute contents, e.g. 10–30% w/v as opposed to 0.5–2%, to produce microparticles comprising low molecular weight active with lactose; active alone: peptides with HSA and modified polymeric carriers with active. We now find that it is the process which dictates the final particle morphology rather than the composition of the solutes. Further, we are able to use combinations of aqueous and water-miscible solvents to enhance particle morphology. Thus we have a "process" driven methodology which allows beneficial production of smooth, spherical controlled sized particles suitable for pulmonary delivery.

It has been found that the process of the invention can be controlled in order to obtain microspheres with desired characteristics. Thus, the pressure at which the protein solution is supplied to the spray nozzle may be varied, for example from $1.0–10.0\times10^5$ Pa, preferably $2–8\times10^5$ Pa, and most preferably about $7.5\times10^5$ Pa. Other parameters may be varied as disclosed below. In this way, novel microspheres may be obtained.

A further aspect of the invention provides hollow microspheres in which more than 30%, preferably more than 40%, 50%, or 60%, of the microspheres have a diameter within a 2 μm range and at least 90%, preferably at least 95% or 99%, have a diameter within the range 1.0–8.0 μm.

The interquartile range may be 2 μm, with a median diameter of 3.5, 4.0, 4.5, 5.0, 5.5, 6.0 or 6.5 μm.

Thus, at least 30%, 40%, 50% or 60% of the microspheres may have diameters within the range 1.5–3.5 μm, 2.0–4.0 μm, 3.0–5.0 μm, 4.0–6.0 μm, 5.0–7.0 μm or 6.0–8.0 μm. Preferably a said percentage of the microspheres have diameters within a 1.0 μm range, such as 1.5–2.5 μm, 2.0–3.0 μm, 3.0–4.0 μm, 4.0–5.0 μm, 5.0–6.0 μm, 6.0–7.0 μm or 7.0–8.0 μm.

A further aspect of the invention provides hollow microspheres with proteinaceous walls in which at least 90%, preferably at least 95% or 99%, of the microspheres have a diameter in the range 1.0–8.0 μm; at least 90%, preferably at least 95% or 99%, of the microspheres have a wall thickness of 40–500 nm, preferably 100–500 nm.

BRIEF DESCRIPTION OF THE DRAWINGS

Preferred aspects of the present invention will be particularly described by way of example and with reference to the accompanying drawings, in which.

DESCRIPTION OF THE INVENTION

Figure 1A:
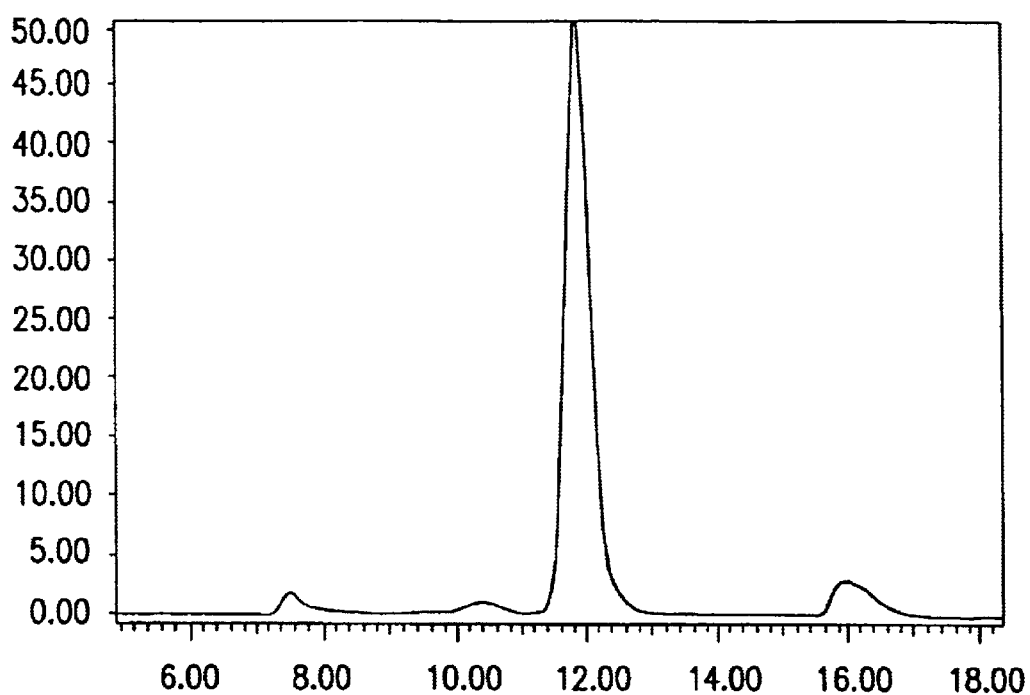
FIGS. 1A and 1B are each overlay chromatograms of HSA before (*) and after spray-drying, respectively from gel-permeation chromatography and reverse-phase HPLC analysis of tryptic digests.

The wall-forming material and process conditions should be so chosen that the product is sufficiently non-toxic and non-immunogenic in the conditions of use, which will clearly depend on the dose administered and duration of treatment. The wall-forming material may be a starch derivative, a synthetic polymer such as tert-butyloxycarbonylmethyl polyglutamate (U.S. Pat. No. 4,888,398) or a polysaccharide such as polydextrose.

Generally, the wall-forming material can be selected from most hydrophilic, biodegradable physiologically compatible polymers. Among such polymers one can cite polysaccharides of low water solubility, polylactides and polyglycolides and their copolymers, copolymers of lactides and lactones such as ε-caperolactone, δ-valerolactone, polypeptides, and proteins such as gelatin, collagen, globulins and albumins. Other suitable polymers include poly-(ortho)esters (see for instance U.S. Pat. No. 4,093,709, U.S. Pat. No. 4,131,648, U.S. Pat. No. 4,138,344, U.S. Pat. No. 4,180,646); polylactic and polyglycolic acid and their copolymers, for instance Dexon (see J. Heller (1980) Biomaterials 1, 51); poly(DL-lactide-co-δ-caprolactone), poly (DL-lactide-co-δ-valerolactone), poly(DL-lactide-co-δ-butyrolactone), polyalkylcyanoacrylates; polyamides; polyhydroxybutyrate; polydioxanone; poly-β-aminoketones (Polymer 23 (1982), 1693); polyphosphazenes (Science 193 (1976), 1214); and polyhydrides. References on biodegradable polymers can be found in R. Langer et al (1983) Macromol. Chem. Phys. C23, 61–125. Polyamino-acids such as polyglutamin and polyaspartic acids can also be used as well as their derivatives, i.e. partial esters with lower alcohols or glycols. One useful example of such polymers is poly(t-butylglutamate). Copolymers with other amino-acids such as methionine, leucine, valine, proline, glycine, alamine, etc. are also possible. Recently some novel derivatives of polyglutamic and polyaspartic acid with controlled biodegradability have been reported (see WO-A-87/03891; U.S. Pat. No. 4,888,398 and EP-A-130935 incorporated here by reference). These polymers (and copolymers with other amino-acids) have formulae of the following type:

—(NH—CHA—CO)₂(NH—CHX—CO)₃ where X designates the side chain of an amino-acid residue and A is a group of formula —(CH$_2$)$_n$COOR$^1$R$^2$OCOR(II), with R$^1$ and R$^2$ being H or lower alkyls, and R being alkyl or aryl; or R and R$^1$ are connected together by a substituted or unsubstituted linking member to provide 5- or 6-membered rings.

A can also represent groups of formulae:

—(CH$_2$)$_n$COO—CHR$^1$COOR   (I)

and

—(CH$_2$)$_n$CO(NH—CHX—CO)$_m$NH—CH(COOH)—CH$_3$)$_p$
COOH   (II)

and corresponding anhydrides. In all these formulae n, m and p are lower integers (not exceeding 5) and x and y are also integers selected for having molecular weights not below 5000.

The aforementioned polymers are suitable for making the microspheres according to the invention and, depending on the nature of substituents R, R$^1$, R$^2$ and X, the properties of the wall can be controlled, for instance, strength, elasticity and biodegradability. For instance X can be methyl (alanine), isopropyl (valine), isobutyl (leucine and isoleucine) or benzyl (phenylalanine).

Preferably, the wall-forming material is proteinaceous. For example, it may be collagen, gelatin or (serum) albumin, in each case preferably of human origin (i.e. derived from humans or corresponding in structure to the human protein). Most preferably, it is human serum albumin (HA) derived from blood donations or, ideally, from the fermentation of microorganisms (including cell lines) which have been transformed or transfected to express HA.

Techniques for expressing HA (which term includes analogues and fragments of human albumin, for example those of EP-A-322094, and polymers of monomeric albumin) are disclosed in, for example EP-A-201239 and EP-A-286424. All references are included herein by reference. "Analogues and fragments" of HA include all polypeptides (i) which are capable of forming a microcapsule in the process of the invention and (ii) of which a continuous region of at least 50% (preferably at least 75%, 80%, 90% or 95%) of the amino-acid sequence is at least 80% homologous (preferably at least 90%, 95% or 99% homologous) with a continuous region of at least 50% (preferably 75%, 80%, 90% or 95%) of human albumin. HA which is produced by recombinant DNA techniques is particularly preferred. Thus, the HA may be produced by expressing an HA-encoding nucleotide sequence in yeast or in another microorganism and purifying the product, as is known in the art. Such material lacks the fatty acids associated with serum-derived material. Preferably, the HA is substantially free of fatty acids; i.e. it contains less than 1% of the fatty acid level of serum-derived material. Preferably, fatty acid is undetectable in the HA.

In the following description of preferred embodiments, the term "protein" is used since this is what we prefer, but it is to be understood that other biocompatible wall-forming materials can be used, as discussed above.

The protein solution or dispersion is preferably 0.1 to 50% w/v, more preferably about 5.0–25.0% protein, particularly when the protein is albumin. About 20% is optimal. Mixtures of wall-forming materials may be used, in which case the percentages in the last two sentences refer to the total content of wall-forming material.

The preparation to be sprayed may contain substances other than the wall-forming material and solvent or carrier liquid. Thus, the aqueous phase may contain 1–20% by weight of water-soluble hydrophilic compounds like sugars and polymers as stabilisers, e.g. polyvinyl alcohol (PVA), polyvinyl pyrrolidone (PVP), polyethylene glycol (PEG), gelatin, polyglutamic acid and polysaccharides such as starch, dextran, agar, xanthan and the like. Similar aqueous phases can be used as the carrier liquid in which the final microsphere product is suspended before use. Emulsifiers may be used (0.1–5% by weight) including most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose.

Additives can be incorporated into the wall of the microspheres to modify the physical properties such as dispersibility, elasticity and water permeability.

Among the useful additives, one may cite compounds which can "hydrophobise" the wall in order to decrease water permeability, such as fats, waxes and high molecular weight hydrocarbons. Additives which improve dispersibility of the microspheres in the injectable liquid-carrier are amphipathic compounds like the phospholipids; they also increase water permeability and rate of biodegradability.

Additives which increase wall elasticity are the plasticisers like isopropyl myristate and the like. Also, very useful additives are constituted by polymers akin to that of the wall itself but with relatively low molecular weight. For instance when using copolymers of polylactic/polyglycolic type as the wall-forming material, the properties of the wall can be modified advantageously (enhanced softness and biodegradability) by incorporating, as additives, low molecular weight (1000 to 15,000 Dalton) polyglycolides or polylactides. Also polyethylene glycol of moderate to low Mw (e.g. PEG 2000) is a useful softening additive.

The quantity of additives to be incorporated in the wall is extremely variable and depends on the needs. In some cases no additive is used at all; in other cases amounts of additives which may reach about 20% by weight of the wall are possible.

The protein solution or dispersion (preferably solution), referred to hereinafter as the "protein preparation", is atomised and spray-dried by any suitable technique which results in discrete microspheres or microcapsules of 1 to 10 $\mu$m diameter. These figures refer to at least 90% of the population of microcapsules, the diameter being measured with a Coulter Master Sizer II. The term "microcapsules" means hollow particles enclosing a space, which space is filled with a gas or vapour but not with any solid materials. Honeycombed particles resembling the confectionery sold in the UK as "Maltesers" (Regd. ™) are not formed.

The atomising comprising forming an aerosol of the protein preparation by, for example, forcing the preparation through at least one orifice under pressure into, or by using a centrifugal atomiser in a chamber of warm air or other inert gas. The chamber should be big enough for the largest ejected drops not to strike the walls before drying. The gas or vapour in the chamber is clean (i.e. preferably sterile and pyrogen-free) and non-toxic when administered into the bloodstream in the amounts concomitant with administration of the microcapsules in use. The rate of evaporation of the liquid from the protein preparation should be sufficiently high to form hollow microcapsules but not so high as to burst the microcapsules. The rate of evaporation may be controlled by varying the gas flow rate, concentration of protein in the protein preparation, nature of liquid carrier, feed rate of the solution and, more importantly, the temperature of the gas encountered by the aerosol. With an albumin concentration of 15–25% in water, an inlet gas temperature of at least about 100° C., preferably at least 110° C., is generally sufficient to ensure hollowness and the temperature may be as high as 250° C. without the capsules bursting. About 180–240° C., preferably about 210–230° C. and most preferably about 220° C., is optimal, at least for albumin. Since the temperature of the gas encountered by the aerosol will depend also on the rate at which the aerosol is delivered and on the liquid content of the protein preparation, the outlet temperature may be monitored to ensure an adequate temperature in the chamber. An outlet temperature of 40–150° C. has been found to be suitable. Controlling the flow rate has been found to be useful in controlling the other parameters such as the number of intact hollow particles.

The microcapsules comprise typically 96–98% monomeric HA.

More particularly, microparticles of the invention preferably have a maximum interquartile range of 3 $\mu$m, more preferably 2 $\mu$m, and most preferably 1.5 $\mu$m, with respect to their mass median particle size. The mass median particle diameter is determined by Coulter counter with a conversion to a volume-size distribution. This is achieved by spray-drying in which there is a combination of low feed stock flow rate with high levels of atomisation and drying air. The effect is to produce microcapsules of very defined size and tight size distribution.

Several workers have designed equations to define the mean droplet size of pneumatic nozzles; a simple version of the various parameters which affect mean droplet size is as follows:

$$D = A/(V^2 \cdot d)^a + B \cdot (M_{air}/M_{liq})^{-b}$$

Where D=Mean droplet size
A=Constant related to nozzle design
B=Constant related to liquid viscosity
V=Relative air velocity between liquid and nozzle
d=Air density
$M_{air}$ and $M_{liq}$=Mass of air and liquid flow
a and b=Constants related to nozzle design Clearly, for any given nozzle design, the droplet size is most affected by the relative velocity at the nozzle and concurrently the mass ratio of air to liquid. For most common drying use, the air to liquid ratio is in the range of 0.1–10 and at these ratios it appears that the average droplet size is 15–20 $\mu$m. For the production of microparticles in the size range described herein we use an air to liquid ratio ranging from 20–1000. The effect is to produce particles at the high ratios which are exceedingly small by comparative standards, with very narrow size distributions. For microparticles, produced at the lower ratios of air to liquid, slightly larger particles are produced, but they still nevertheless have tight size distributions which are superior to microparticles produced by emulsion techniques.

The amount of the active principle is not critical; the microparticles may comprise at least 50, more preferably 70 or 80, and most preferably 90, % by weight HSA or other carrier material. For use in an inhaler device, the microparticles may be formulated with a conventional excipient such as lactose or glucose.

The microparticles may comprise therapeutic agent and carrier, or a compound which alone is therapeutically-active. The amount of the active principle will be chosen having regard to its nature and activity, to the mode of administration and other factors known to those skilled in the art. By way of example only, the number of particles administered may be such as to deliver 100 mg/day α-1 anti-trypsin, or 0.1 mg/day of an active material such as beclomethasone.

The active principle may be, for example, a diagnostic substance or a classical pharmaceutical entity which may or may not bind, covalently or otherwise, to the carrier material. The therapeutic agent may be a proteinaceous material such as insulin, parathyroid hormone, calcitonin or similar bioactive peptide, albuterol, salicylate, naproxen, augmentin or a cytotoxic agent. For experimental purposes, a marker such as lysine-fluorescein may be included.

Microparticles of the invention may comprise an antagonist or receptor-binding component in addition to the therapeutic or diagnostic agent. For example, a sugar or other molecule may be included in the molecular vehicle, with a view to directing administration of the vehicle-bound drug to a given receptor at or beyond the alveoli.

HSA is used herein as an illustrative example of water-soluble carrier materials for use in the invention. Other materials that can be used include simple and complex carbohydrates, simple or complex amino- or polyamino-acids, fatty acid or fatty acid esters, or natural or recombinant human proteins or fragments or short forms thereof.

The invention allows for the nature of the dry microcapsules to be manipulated, in order to optimise the flow or vehicle properties, by changing and reducing the forces of cohesion and adhesion within the microcapsule preparation. For example, if so required, the microcapsules may be made predominantly positive or negative by the use of highly-charged monomeric or polymeric materials, e.g. lysine or poly-lysine and glutamate or poly-glutamate in systems without HSA or heterogeneous systems including HSA and active principles.

A further embodiment of the invention is the co-spray-drying of the active principle with HSA in order to facilitate stabilisation of the active principle during formulation, packing and, most importantly, during residence on the alveolar lining. In this environment, there can be intense proteolytic activity. Whilst protease inhibitors can be used to protect peptide drugs, there may well be contra-indications to this approach. By using HSA, both as excipient and vehicle, it can offer a large excess of alternative substrate on which the locally-active proteases may act. A further advantage is that, since HSA has been shown to cross the alveolar barrier, by receptor- or non-receptor-mediated transcytotic mechanisms, it may be used as a vehicle to facilitate the passage of an active principle across the endothelial lining.

In a further embodiment, active principle may be covalently linked to HSA via cleavable linkages prior to spray-drying. This embodiment represents a method of carrying active principles all the way from device to bloodstream, and possibly to targets within the body. The formation of particles with optimal aerodynamic size means that the "physical" vehicle delivers the active principle to the site of absorption. Once deposited upon the alveoli, the "molecular" vehicle then protects and facilitates passage into the bloodstream and, once in the bloodstream, can further enhance circulatory half-life and even direct the active principle to certain sites within the body on the basis of receptor-mediated events.

A suitable linker technology is described in WO-A-9317713 (Rijksuniversiteit Groningen). Esterase-sensitive polyhydroxy acid linkers are described. Such technology, used in the derivatisation of HSA prior to spray-drying, enables the production of a covalent carrier system for delivery of drugs to the systemic vasculature. This utilises the potential of HSA to cross the alveoli to carry drugs over a prolonged period whilst protecting potentially unstable entities.

Although the active principle used in this invention may be imbibed into or otherwise associated with the microparticles after their formation, it is preferably formulated with the HSA. The microparticles may be at least partly coated with a hydrophobic or water-insoluble material such as a fatty acid, in order to delay their rate of dissolution and to protect against hydroscopic growth.

Figure 4:
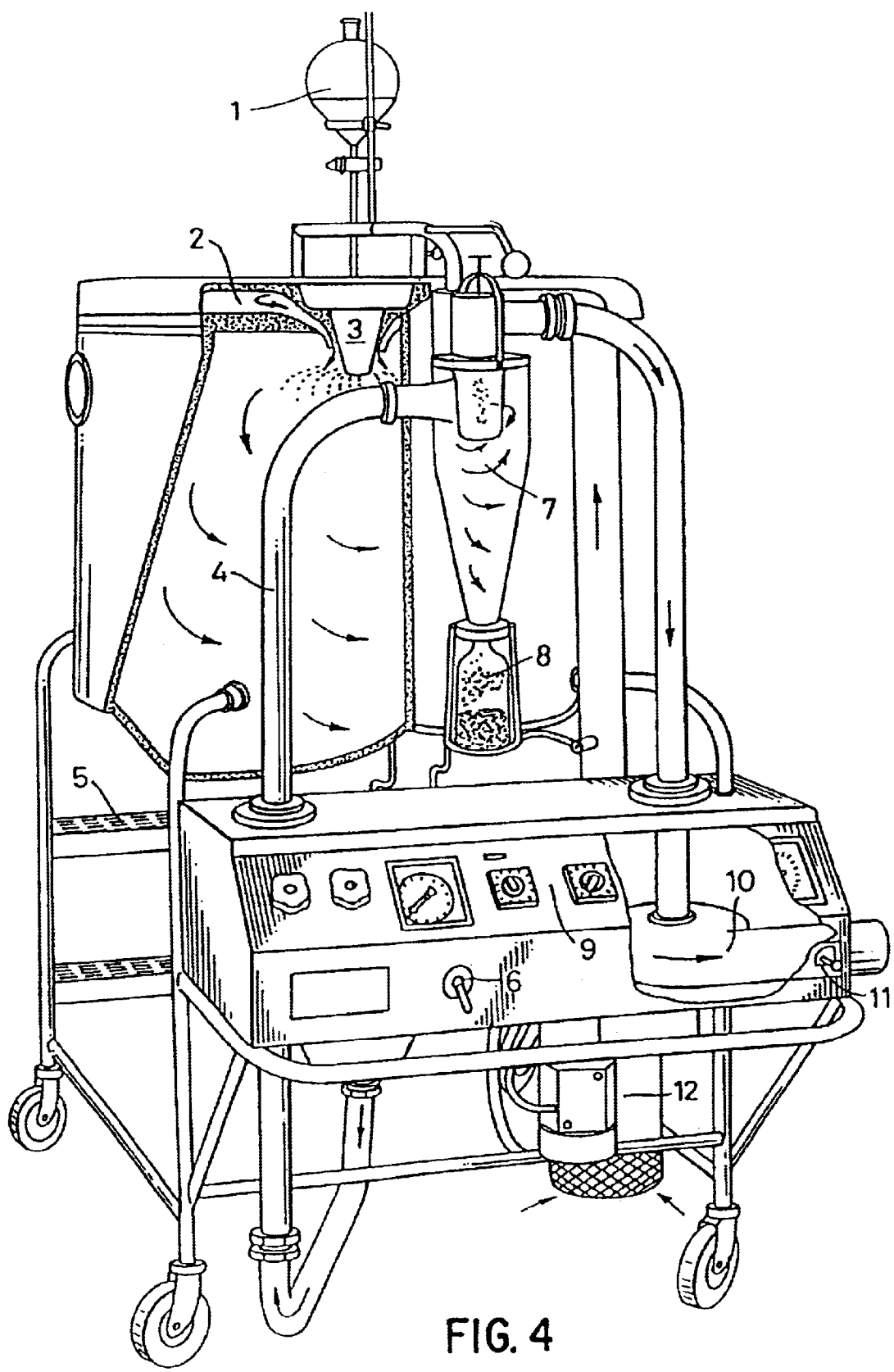
FIG. 4 is a partly cut-away perspective view from the front and one side of suitable spray-drying apparatus for use in the process of the invention.

The following Examples illustrate the invention. The spray dryer used in the Examples and shown in FIG. 4 is available from A/S Niro Atomizer, Soeborg, Denmark, under the trade name "Mobile Minor". Details of its construction will now be given.

FIG. 4 shows a feeding device 1 and a ceiling air dispenser 2 which ensures effective control of the air flow pattern. Swirling air is directed around the vaned disc atomiser. 3 is a rotary atomiser or nozzle atomiser. 4 shows a stainless steel interconnecting pipe system which can easily be stripped down for cleaning. 5 are steps for access to the chamber top. 6 is the switch for an air valve for activation of the pneumatic lifting device when raising the chamber lid. 7 is a highly-efficient stainless steel cyclone in which the powder and the exhausted drying air are separated. 8 is a glass jar in which the powder is recovered. 9 is a centrally located instrument panel. 10 is a centrifugal exhaust fan with three-phase motor. 11 is a damper for air flow control and 12 is an electric air heater which provides drying air temperatures up to 350° C. The drying air temperature can be continuously adjusted using a percentage timer switch. The maximum powder consumption is 7.6 kW.

| Drying Air | Evaporative capacity | | |
|---|---|---|---|
| | Inlet Air Temperature | Outlet Air Temperature | Evaporative Capacity |
| 85 kg/h | 150° C. | 80° C. | 1.3 kg/h |
| 85 kg/h | 170° C. | 85° C. | 1.7 kg/h |
| 80 kg/h | 200° C. | 90° C. | 2.5 kg/h |
| 80 kg/h | 240° C. | 90° C. | 3.4 kg/h |
| 75 kg/h | 350° C. | 90° C. | 7.0 kg/h |

| Weight and dimension | |
|---|---|
| Weight | 280 kg |
| Length | 1800 mm |
| Height | 2200 mm |
| Width | 925 mm |

Power

The unit can only be operated on a three-phase power supply (50 or 60 Hz) at alternative voltages of 440, 415, 400, 380, 220, 220 V.

The "Mobile Minor" comprises a centrifugal atomizer (Type M-02/B Minor), driven by an air turbine at an air pressure of min 4 bar and up to max 6 bar. At 6 bar an atomizer wheel speed of approx 33,000 rpm is reached. Turning on and off the compressed air to the atomizer is done by means of a valve placed in the instrument panel. The maximum consumption of compressed air to the atomizer is 17 Nm3/h at a pressure of 6 bar. All parts coming into contact with the liquid feed and powder are made of stainless steel AISI 316, except for the pump feed tube and the atomizer wheel, which is made of stainless steel AISI 329, made to resist high centrifugal force.

The drying chamber has an inside made of stainless steel AISI 316, well insulated with Rockwool, and covered outside with a mild steel sheeting. The drying chamber is provided with a side light and observation pane for inspection during the operation. The roof of the drying chamber is made inside of stainless steel AISI 316 and outside of stainless steel AISI 304.

An air disperser made of stainless steel AISI 304 is used for distribution of the air in the drying chamber in order to achieve the best possible drying effect. An air duct, made of stainless steel AISI 316, provides lateral transportation of the exhaust air and the powder to the cyclone, which is made of stainless steel AISI 316 and designed to separate the powder and air.

A closing valve of the butterfly valve type, also made of stainless steel AISI 316 and having a gasket of silicone rubber, is used for powder discharge under the cyclone into a powder collecting glass jar tightly placed under the cyclone by means of a spring device.

A fan made of silumin, complete with 3-phase squirrel-cage motor, 0.25 kW, and V-belt drive with belt-guard, draws air and powder through the drying chamber and cyclone.

An air heater heats the drying air by means of electricity (total consumption 7.5 kWh/h, infinitely variable) and can give inlet air temperatures of up to about 350° C., although this is generally too high for preparing the microcapsules of the invention.

Equipment for two-fluid nozzle atomisation may be added, which is made of stainless steel AISI 316, consisting of entrance pipe with nozzle holder, to be placed in the ceiling of the drying chamber. The equipment includes an oil/water separator, reduction valve and pressure gauge for compressed air to the two-fluid nozzle. Consumption of compressed air: 8–15 kg/h at a pressure of 0.5–2.0 bar ($0.5$–$2.0 \times 10^5$ Pa).

A suitable feed pump for transport of wall-forming preparation feed to the atomizer device is a peristaltic pump. The pump is provided with a motor (1×220 V, 50 Hz, 0.18 kW) and a continuously variable gear for manual adjustment. A feed pipe made of silicone hose leads from a feed tank (local supply) through the feed pump to the atomization device. An absolute air filter, consisting of prefilter, filter body in stainless steel and absolute air filter, is used for the treatment of the ingoing drying air to render it completely clean.

EXAMPLE 1

A 20% solution of sterile, pyrogen-free HSA in pyrogen-free water (suitable for injection) was pumped to the nozzle of a two-fluid nozzle atomizer mounted in the commercial spray-drying unit described above. The peristaltic pump speed was maintained at a rate of approximately 10 ml/minute such that with an inlet air temperature of 220° C. the outlet air temperature was maintained at 95° C.

Compressed air was supplied to the two fluid atomising nozzle at 2.0–6.0 Bar ($2.0$–$6.0 \times 10^5$ Pa). In this range microcapsules with a mean size of 4.25–6.2 $\mu$m are obtained.

Typically an increase in mean particle size (by reduced atomisation pressure) led to an increase in the amount of microcapsules over 10 $\mu$m in size (see Table 1).

TABLE 1

| Effects of Atomisation Pressure on Frequency of Microcapsules Over 10 $\mu$m in Diameter | |
|---|---|
| Atomisation Pressure (× $10^5$ Pa) | % Frequency over 10 mm |
| 6.0 | 0.8 |
| 5.0 | 3.3 |
| 3.5 | 6.6 |
| 2.5 | 8.6 |
| 2.0 | 13.1 |

Figure 1B:
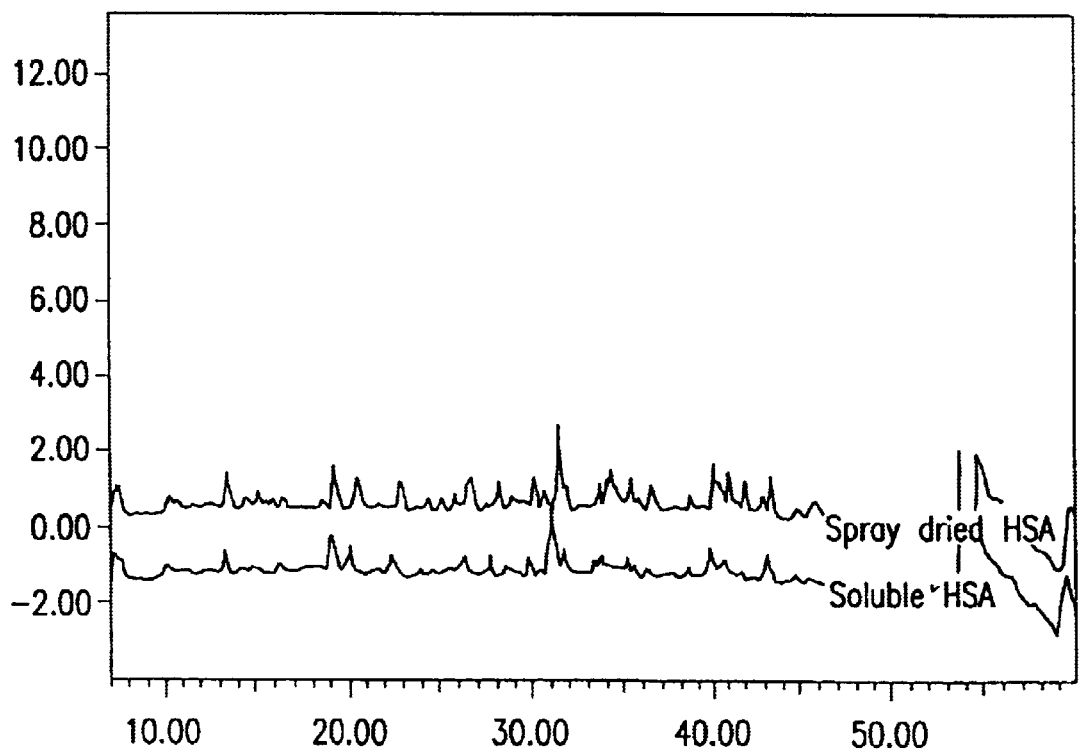

Under the conditions described, with a nozzle pressure of 7.5 bar, microparticles were produced with a particle size of 4.7 $\mu$m. These soluble microparticles were smooth and spherical with less than 1% of the particles over a particle size of 6 $\mu$m. The microparticles were dissolved in aqueous medium and the molecular weight of the HSA determined by gel filtration chromatography. The resultant chromatograms for the original and spray-dried HSA are shown (FIG. 1). Further analysis of the HSA before and after spray-drying by means of tryptic peptide mapping with HPLC revealed that there were no observable differences in the peptides liberated (FIG. 1). Both analysis show, that under the conditions of spray-drying described to produce microparticles of 4.7 μm, little or no structural damage is done to the protein.

EXAMPLE 2

Alpha-1 antitrypsin derived from human serum was spray-dried under conditions similar to Example 1 with an inlet temperature of 150° C. and an outlet temperature of 80° C. In all other respects the conditions for drying were the same as Example 1. The soluble microparticles produced had a mean size of 4.5 μm. The microparticles were dissolved in aqueous medium and analysed for retention of protein structure and normal trypsin inhibitory activity, then compared to the original freeze dried starting material. Analysis by gel permeation and reverse phase chromatography and capillary electrophoresis, revealed that there were no significant structural changes after spray-drying. Analysis of the inhibitory activity (Table 2) showed that within the experimental error, full retention of inhibitory activity had been achieved.

TABLE 2

| Run Number | Percentage of Activity Retained |
| --- | --- |
| 1 | 84 |
| 2 | 222 |
| 3 | 148 |

EXAMPLE 3

Using the general method of Example 1, microcapsules composed of alcohol dehydrogenase (ADH) and lactose were prepared (ADH 0.1% w/w; Lactose 99.9% w/w). We find that optimisation of the spray-drying step is required to maximise the retention of enzyme activity. The general conditions of Example 1 were used, but the inlet and outlet temperature were changed to give conditions which allowed us to produce microparticles of the desired size (4–5 μm) that retained full activity after drying and reconstitution in aqueous media. The percentage of activity retained compared with the original material is shown for each of the spray-drying conditions shown (Table 3). The microcapsules were smooth and spherical and contained air as evidenced by their appearance in diphenylxylene (DPX) under light microscopy.

TABLE 3

| Run | Inlet Temp. ° C. | Outlet Temp. ° C. | Activity Remaining (%) |
| --- | --- | --- | --- |
| 1 | 220 | 73 | 57 |
| 2 | 175 | 71 | 98 |

EXAMPLE 4

A series of experiments was performed under the conditions described in Example 1, to examine the influence of liquid feed rate on the yield of intact spherical particles. We find that, using the ability of gas-containing microparticles to reflect ultrasound, we are able to determine optimal condition for maximising the yield of intact smooth spherical microcapsules. The microparticles formed after spray-drying are heat-fixed, to render them insoluble, and then suspended in water to make the echo measurements. We find that increasing the liquid feed rate decreases the number of intact microparticles formed during the initial spray-drying (Table 4). The mean particle size and overall pressure stability, i.e. thickness of the shell, do not change but the total echogenicity does, as the liquid flow rate is increased from 4 to 16 ml/min. We find that slower rates of evaporation (at higher liquid flow rates) lead to fewer intact spherical particles being formed.

TABLE 4

| Flow Rates (ml/min) | 4 | 8 | 12 | 16 |
| --- | --- | --- | --- | --- |
| Mean size (μm) | 3.08 | 3.04 | 3.13 | 3.07 |
| Echogenicity (video density units) | 22 | 21 | 14 | 10 |
| Echogenicity after pressure (video density units) | 20 | 18 | 10 | 8 |

Figure 3:
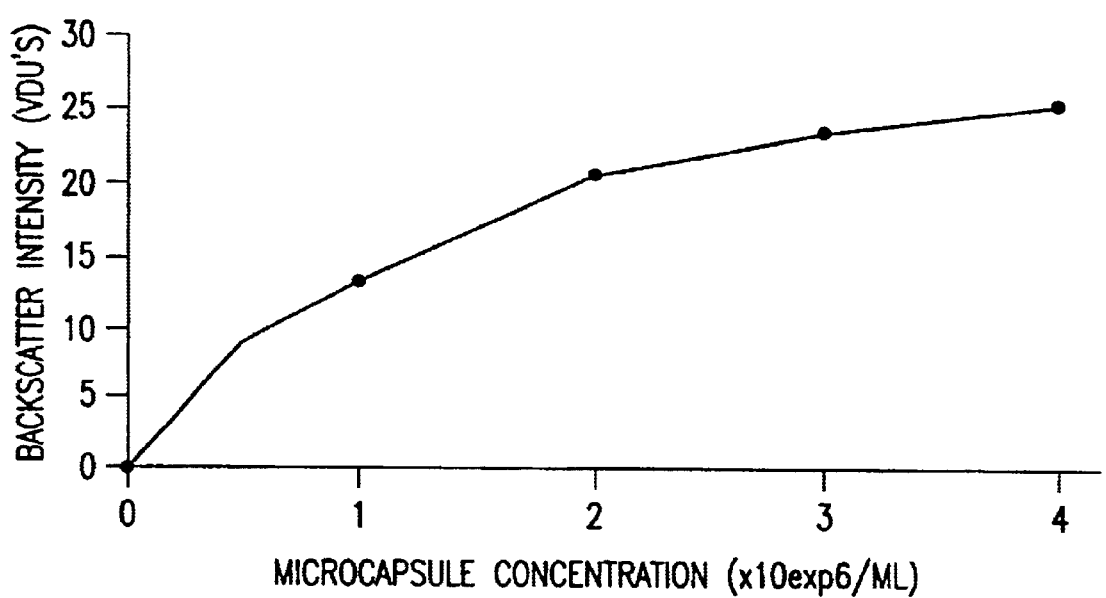
FIG. 3 is an ultrasound dose-response curve for microparticles manufactured in accordance with Example 1.

The assay was conducted by resuspending the heat-fixed microparticles at a concentration of $1 \times 10^6$ ml in 350 ml of water. This solution is stirred slowly in a 500 ml beaker above which is mounted an 3.5 MHz ultrasound probe attached to a Sonus 1000 medical imaging machine. The grey scale images obtained are captured by an image analyser and compared against a water blank to yield video density units of echo reflectance. The assay can also be adapted to examine the pressure resistance, by assessing the echo-reflectance before and after exposure of the sample to cyclical bursts of pressure applied to the stock solution of particles. This analysis distinguishes incomplete particles which entrain air upon reconstitution, from fully spherical particles which "encapsulate" air within the shell. Incomplete particles do not show pressure resistance and lose the ability to reflect ultrasound immediately. The dose response for fixed albumin particles of Example 1 is shown in FIG. 3.

EXAMPLE 5

Significant experimentation to reduce the particle size and narrow the size distribution has been performed. This was pursued to effectively increase the gas content of the echo-contrast agent and reduce the number of oversized particles. This exercise is also beneficial to respiratory formulations in that it maximises the potential number of respirable particles in the 1–5 μm range and produces inherently more smooth particles which will be less cohesive than non spherical particles of similar size.

Figure 2:
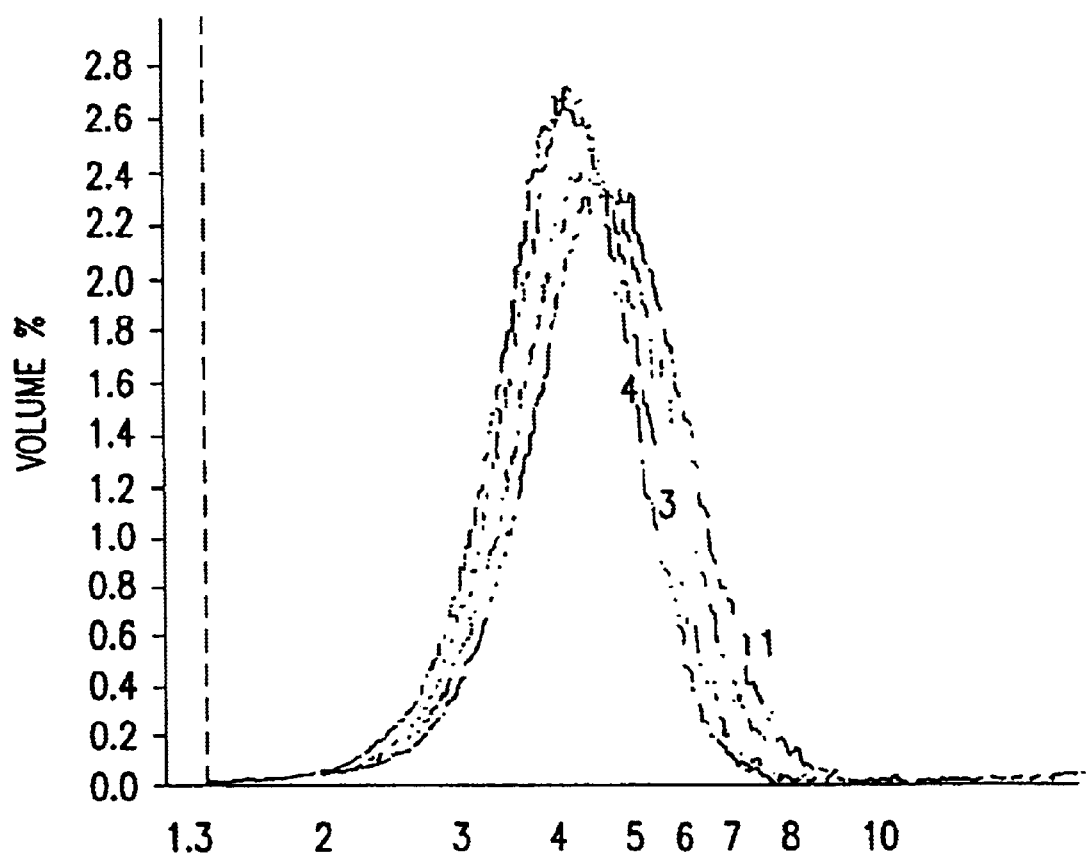
FIG. 2 is a plot of volume with respect to size, showing the size control of microparticles by manipulation of solute concentration, from feedstocks containing 1) 15% w/v, 2) 12.5% w/v, 3) 10% w/v, and 4) 7.5% w/v HSA (analysis of fixed particles by Coulter counting)

We find that it is possible to reduce particle size by lowering the solutes content of the feedstock (FIG. 2). This effect, is in part, mediated by the effects of viscosity on droplet formation. However, we also find that by lowering the solute content under the conditions we use leads to a significant decrease in the number of intact particles. By further experimentation we have found that incorporation of water miscible, volatile solvents in the feedstock, significantly increase the rate of shell formation during drying, with a concomitant increase in the number of intact particles or hollow particles (Table 5). The assessment of hollowness is made by microscopic evaluation of particles floating to the surface of the coverslip on a haemocytometer versus particle count by Coulter counting.

TABLE 5

| Run | HSA Content of Feedstock (%) | Ethanol Content of Feedstock (%) | Mean Particle Size (μm) | Percentage of Hollow Particles (%) |
|---|---|---|---|---|
| 1 | 10 | 0 | 3.7 | 12.5 |
| 2 | 10 | 25 | 3.52 | 64.3 |

EXAMPLE 6

A range of materials has been used to manufacture smooth spherical soluble microparticles. The range of microparticles produced includes inert materials such as HSA, lactose, mannitol, sodium alginate; active materials alone such as α1-antitrypsin; and mixtures of active and inert carrier such as lactose/alcohol dehydrogenase, lactose/budesonide, HSA/salbutamol. In all cases smooth spherical and gas containing particles are produced. We have assessed the success of the process in maintaining control over the morphology of the particles produced by microscopy. The particles are suspended in propanol and then visualised by microscopy. Those particles which contain gas appear to have an intense white core surrounded by an intact black rim whilst broken or miss-formed particles appear as ghosts. Microscopic evaluation of the following microparticles exemplifies the range of materials and actives which can be dried to produce smooth spherical particles.

HSA

Casein

Haemoglobin

Lactose

ADH/lactose

HSA/Peroxidase

Lactose/Salbutamol

Lactose/Budesonide

EXAMPLE 7

Lactose and Budesonide were spray-dried under the conditions described in the table below (Table 6).

TABLE 6

| Parameter | Setting |
|---|---|
| Inlet Temperature | 220° C. |
| Outlet Temperature | 85° C. |
| Atomisation Pressure | 7.5 bar |
| Damper Setting | 0.5 |
| Feed Rate | 3.88 g/min |
| Stock Solution | 9.3% w/v Budesonide, 85% v/v Ethanol 19% w/v lactose |

The resultant dry powder was blended with excipient grade lactose in a V type blender in the proportions outlined in Table 7. The blends were then loaded into gelatin capsules and discharged from a Rotahaler™ into a twin stage impinger run at 60 l/min. The respirable fraction was calculated as the percentage deposited into the lower chamber.

TABLE 7

| Formulation Number | % Budesonide in spray dried particles | % spray dried product in blend | % fast flow lactose in blend | Respirable fraction |
|---|---|---|---|---|
| 1 | 9.3 | 10 | 90 | 42 |
| 2 | 9.3 | 15 | 85 | 29 |
| 3 | 9.3 | 20 | 80 | 34 |
| 4 | 5.7 | 30 | 70 | 36 |

The respirable fractions obtained are considerably superior to micronised product currently used in this device which are usually in the range of 10–20% maximum.

The Budesonide/Lactose formulations detailed in Example 7 were tested in an experimental gravity fed multi-dose DPI. The parameters examined were the variation of emitted dose over 30 shots and the respirable fraction in a four stage impinger device. The results are shown below (Table 8).

TABLE 8

| Formulation Number | Dose (mg) | Fine Particle (Respirable) Fraction (%) | CofV on Emitted Dose (%) |
|---|---|---|---|
| 1 | 4 | 52 | 2.0 |
| 2 | 4.2 | 42 | 2.8 |
| 3 | 3.7 | 58 | 8.1 |

For current DPI devices the US Pharmacopoeia states less than 10% variation in the emitted dose. Clearly in all of the formulations tested so far we are within the current specifications and in the case of formulations 1 and 2 we are significantly under the current limits.

EXAMPLE 8

To decrease the dissolution rate of soluble microcapsules as described in preceding Examples, microcapsules may be coated with fatty acids such as palmitic or behenic acids. The soluble microcapsules of Example 1 were coated by suspending a mixture of soluble HSA microcapsules and glucose (50% w/w) in an ethanolic solution containing 10% palmitic or behenic acid. The solution was evaporated and the resultant cake milled by passage through a Fritsch mill.

The efficacy of coating was assessed by an indirect method derived from our previous ultrasound studies. Ultrasound images were gathered from a beaker of water containing $1 \times 10^6$ microcapsules/ml using a HP Sonus 1000 ultrasound machine linked to an image analyser. Video intensity over a blank reading (VDU) was measured over time (Table 9).

The uncoated microcapsules very quickly lost all air and thus the potential to reflect ultrasound. However, coated microcapsules retained their structure for a longer period and hence showed a prolonged signal over several minutes.

TABLE 9

Echogenicity of Coated HSA Microcapsules

| | Echogenicity (VDU) | | |
|---|---|---|---|
| Time (min) | HSA only | HSA/Palmitic Coated | HSA/Behenic Coated |
| 0 | 1.75 | 1.91 | 0.88 |
| 5 | 0.043 | 0.482 | 0.524 |
| 10 | 0 | 0 | 0.004 |

EXAMPLE 9

Soluble mannitol microcapsules were prepared as set out in Example 1 (15% aqueous mannitol spray-drying feedstock) and coated with palmitic acid and behenic acid as described in Example 8. A sample of each was suspended in water and the echogenicity measured. Ten minutes after the initial analysis, the echogenicity of the suspended samples was repeated (Table 10).

TABLE 10

Echogenicity of Coated Mannitol Microcapsules

| | Echogenicity (VDU) | | |
|---|---|---|---|
| Time (min) | Mannitol | + Palmitic | + Behenic |
| 0 | 1.6 | 1.7 | 0.92 |
| 10 | 0.33 | 0.5 | 0.24 |
| 17 | 0 | 0.84 | 0 |

EXAMPLE 10

Soluble microcapsules with a model active (Lysine-Fluoroscein) contained within the matrix were prepared to allow the production of a free flowing dry powder form of the "active" compound. On dissolution of the microcapsules the active compound was released in its native form.

Using lysine as a model compound, the molecule was tagged with fluorescein isothiocyanate (FITC) to allow the compound to be monitored during the preparation of the soluble microcapsules and the subsequent release during dissolution.

3 g of lysine was added to FITC (0.5 g total) in carbonate buffer. After one hour incubation at 30° C., the resultant solution was tested for the formation of the FITC-lysine adduct by TLC. This showed the presence of a stable FITC-lysine adduct.

The FITC-lysine adduct was mixed with 143 ml of 25% ethanol containing 100 mg/ml HSA to give the spray-drying feedstock. The spray-drying conditions used to form the microcapsules are detailed in Table 11 below. In the absence of ethanol we have found that only a small percentage of the particles are smooth and spherical.

The spray-drying process produced 17.21 g of microcapsules that did not dissolve when a sample was resuspended in ethanol. Moreover, no release of the FITC-lysine adduct was observed. However, when 10 ml water was added to the ethanol-suspended microcapsules, the microcapsules dissolved and the FITC-lysine was released. Analysis of the adduct using TLC before incorporation into the microcapsules and after release from the microcapsules on dissolution showed the model compound was unchanged.

TABLE 11

Spray-Drying Conditions

| Parameter | Setting |
|---|---|
| Inlet Temperature | 220° C. |
| Outlet Temperature | 85° C. |
| Atomisation Pressure | 7.5 bar |
| Damper Setting | 0.5 |
| Feed Rate | 3.88 g/min |
| Stock Solution | 25% v/v Ethanol, 10% w/v HSA |

The soluble microcapsules were sized in a non-aqueous system of ammonium thiocyanate and propan-2-ol using a Multisizer II (Coulter Electronics). The microcapsules had a mean size of 3.28 n 0.6 $\mu$m and with 90% of the mass within 2–5 $\mu$m.

The microcapsules were mixed with glucose (50% w/w microcapsules:50% w/w glucose), and milled by the passage of the mixture through a Fritsch mill three times. When a sample of the powder was added to water, the FITC-lysine was released intact when compared with its original form as determined by TLC analysis. This example shows the feasibility of making an amino acid or peptide formulation which could be used for respiratory formulations, which incorporates HSA within the formulation.

EXAMPLE 11

500 mg beclomethasone was dissolved in ethanol and added to 50 ml HSA feedstock (10% w/v) and spray-dried using the conditions outlined in Example 10. The microcapsules hence formed were sized in the no-aqueous system as detailed in Example 10. The microcapsules had a mean size of 3.13±0.71 $\mu$m, 90% of which were between 2 and 5 $\mu$m.

The beclomethasone was extracted from the microcapsules by the precipitation of the HSA in 10% TCA, and the supernatant was extracted into ethanol. The ethanol extract was analysed using HPLC, at a wavelength 242 nm. The beclomethasone detected in this extract exists in the free state, but when the albumin pellet was extracted the presence of beclomethasone bound to native HSA was observed. It was found that although the majority of the active compound was in the free state, some was present in the albumin-bound state. Since albumin partitions only slowly into the bloodstream, this allows control over the release of the active compound over an extended period of time, compared to free drug.

EXAMPLE 12

Whereas in Examples 10 and 11 at least, any binding of the active compounds was an effect of the intrinsic nature of albumin, this Example gives a product following initial cross-linking of the active compound, prior to spray-drying.

To a 10 mg/ml solution of methotrexate, 25 mg carbodiimide (EDCI) was added. The solution was stirred for 4 hours to initiate and ensure complete activation of the methotrexate. 50 mg BSA was added to the activated drug and stirred for 3 hours at room temperature. The methotrexate is chemically bound to the HSA via the amine groups on the albumin. This conjugate was then used as the spray-drying feedstock as detailed in Example 10.

The soluble microcapsules thus made were sampled, characterised and analysed for drug content. The microcapsules had a mean size of 3.2±0.6 $\mu$m with 90% by mass between 2–5 μm. The analysis of the drug content of the microcapsules showed that the microcapsules did not release drug; even after dissolution, drug was still bound to the HSA. Proteinase K digestion of the albumin released the bound drug which was shown to be linked to only a limited number of amino-acids and small peptides. It has been shown previously that the activity of doxorubicin bound to polymeric carriers proves beneficial in tumours showing the multidrug-resistant phenotype.

EXAMPLE 13

Naproxen microcapsules were prepared as detailed in Examples 10 and 12 using a ratio of 1 to 5, drug to HSA. The soluble microcapsules retained the active compound of a non-aqueous solvent. Moreover, on dissolution of the microcapsules in aqueous solution, the active compound was still bound to the albumin, as shown by HPLC analysis at 262 nm, as before. The naproxen was released from the albumin on digestion with proteinase K and esterases.

EXAMPLE 14

To decrease the dissolution rate of soluble HSA microcapsules as formed in Examples 10 to 13, microcapsules were coated with palmitic or behenic acids. The microcapsules were coated by suspending a mixture of soluble HSA microcapsules and glucose (50% w/w) in an ethanolic solution containing 10% palmitic or behenic acid. The solution was evaporated and the resultant cake milled by passage through a Fritsch mill.

The efficacy of coating was assessed by an indirect method derived from our previous ultrasound studies. The hollow nature of the microcapsules means that an echo signal may be obtained by reflection from the suspended air bubbles using echogenic assay developed for our ultrasound contrast agent. Ultrasound images were gathered from a beaker of water containing $1 \times 10^6$ microcapsules/ml using a HP Sonus 1000 ultrasound machine linked to an image analyser. Video intensity over a blank reading (VDU) was measured over time.

The uncoated microcapsules very quickly lost all air and thus the potential to reflect ultrasound. However, as shown in Table 12, coated microcapsules retained their structure for a longer period and hence showed a prolonged signal over several minutes.

TABLE 12

Echogenicity of Coated HSA Microcapsules

| Time (min) | HSA only | HSA/Palmitic | HSA/Behenic |
| --- | --- | --- | --- |
| 0 | 1.750 | 1.911 | 0.878 |
| 5 | 0.043 | 0.482 | 0.524 |
| 10 | 0 | 0 | 0.004 |

EXAMPLE 15

Soluble mannitol microcapsules were prepared as set out in Example 10 (15% aqueous mannitol spray-drying feedstock) and coated with palmitic acid and behenic acid as described in Example 14. A sample of each was suspended in water and the echogenicity measured. Ten minutes after the initial analysis, the echogenicity of the suspended samples was repeated. The results are shown in Table 13.

TABLE 13

Echogenicity of Coated Mannitol Microcapsules

| Analysis Time | Mannitol | Mannitol/Palmitic | Mannitol/Behenic |
| --- | --- | --- | --- |
| 0 | 1.632 | 1.732 | 0.924 |
| 10 min | 0.325 | 0.502 | 0.235 |
| 17 hours | 0.00 | 0.842 | not determined |

EXAMPLE 16

Using samples of the microcapsules produced in the Examples 10 to 18, an assessment of their behaviour in a dry powder inhaler was made. The dosing reproducibility of each formulation was assessed in conjunction with the aerolisation of the sample by microscopic evaluation.

A sample of each formulation was added to the storage funnel of an experimental dry powder inhaler (DPI). The dry powder inhaler used pressurised air to force the powder into a dosing measure. The dosing measure used was calibrated using spray-dried lactose.

Although the amounts dispensed into the dosing measure varied between samples as a function of their composition, the dosing reproducibility for each sample was very consistent; with a mean of 5.0±0.25 mg obtained for three dosing trials.

The aerolisation behaviour of the samples was tested by connecting the inhaler to a vacuum chamber; simulated inhalation was achieved by the release of the vacuum through the DPI and collection of the airborne dose was made on resin coated microscope slides. These slides were evaluated for dispersion of the particles. The slides showed that the DPI had deagglomerated the samples forming an even dispersion of microparticles on the microscope slides.

EXAMPLE 17

The performance of the dry powder formulations from Examples 10 to 13 was analysed using the twin impinger method (Apparatus A for pressurised inhalations, British Pharmacopoeia 1988) following discharge from a Rotahaler (Glaxo UK) with 7 ml in stage 1 and 30 ml in stage 2 of distilled water. The formulations were delivered from size 3 gelatin capsules using a Rotahaler attached to the twin impinger using a rubber adapter. The vacuum pump was operated at 60 l/min for two 3 second bursts. The amount of each sample reaching stage 1 and stage 2 levels of the impinger was analysed. All samples showed the largest percentage deposition to occur in stage 2 of the impinger indicating optimal sized particles for alveoli delivery.

EXAMPLE 18

A comparison of the dosing and deposition of fixed insoluble microcapsules and soluble microcapsules as produced in Example 10 was made in the lung of rabbits.

Anaethestised New Zealand white rabbits were dosed either with soluble microcapsules or fixed microcapsules. The dosing was carried out using a computer controlled nebuliser (Mumed Ltd., UK). The soluble microcapsules were suspended in CFC 11 and the fixed particles were suspended in water. After dosing, the lungs of the rabbits were removed and an assessment of the deposition of the capsules made.

The fixed capsules were found intact in the alveoli tissue of the lung. This showed that the microcapsules were of the appropriate size for dispersion through the lungs. In comparison, no evidence of the presence of intact soluble microcapsules was found, the capsules having dissolved in the fluids of the lung. However, the presence of FITC-lysine adduct was observed in some of the alveoli tissue when studied using fluorescent microscopy. In addition, the presence of the adduct was also found the blood and urine of the animals, as opposed to that of the fixed capsules which showed no presence in either.

What we claim is:

1. A therapeutic composition for administration via the pulmonary airways comprising substantially dry, discrete microcapsules having a solid wall formed of a non-denatured, water-soluble wall-forming material, wherein the wall-forming material is a protein, peptide, or enzyme, and wherein said microcapsules have a mean size of between 1 and 10 $\mu$m, and a therapeutically effective amount of a therapeutic agent;

wherein the wall forming material optionally is the therapeutic agent.

2. The composition according to claim 1, wherein said therapeutic agent is the sole component of the microcapsule.

3. The composition according to claim 1, wherein the particle size of said microcapsule is between 1 and 5 $\mu$m.

4. The composition according to claim 1, wherein said microcapsules have a maximum interquartile range of 3 $\mu$m.

5. The composition according to any of claims 1 to 4, which is sterile.

6. The composition according to claim 2, wherein the particle size of said microcapsule is between 1 and 5 $\mu$m.

7. The composition according to claim 2, wherein said microcapsules have a maximum interquartile range of 3 $\mu$m.

8. The composition according to claim 2, wherein said microcapsules have a maximum interquartile range of 2 $\mu$m.

9. The composition according to any of claims 6–8, which is sterile.

10. The composition according to claim 2, wherein said water-soluble material is a human protein or fragment or recombinant thereof.

11. The composition according to claim 2, wherein said water-soluble material is a protein with a NH, CO, OH or SH retained functional group.

12. The composition according to claim 1, wherein said microcapsules have a maximum interquartile range of 2 $\mu$m.

13. The composition according to claim 1, wherein said water-soluble material is a human protein or fragment or recombinant thereof.

14. The composition according to claim 1, wherein said water-soluble material is a protein with a NH, CO, OH or SH retained functional group.

15. A therapeutic or diagnostic composition for administration via the pulmonary airways comprising substantially dry, discrete microcapsules having a solid wall formed of a non-denatured, water-soluble wall-forming material, wherein the wall-forming material is an amino or polyamino acid, and wherein said microcapsules have a mean size of between 1 and 10 $\mu$m, and an effective amount of a therapeutic or diagnostic agent;

wherein the wall forming material optionally is the therapeutic or diagnostic agent.

16. The composition according to claim 15, wherein said therapeutic or diagnostic agent is the sole component of the microcapsule.

17. The composition according to claim 15, wherein the particle size of said microcapsule is between 1 and 5 $\mu$m.

18. The composition according to claim 15, wherein said microcapsules have a maximum interquartile range of 3 $\mu$m.

19. The composition according to claim 15, wherein said microcapsules have a maximum interquartile range of 2 $\mu$m.

20. The composition according to claim 15, which is sterile.

* * * * *

UNITED STATES PATENT AND TRADEMARK OFFICE
CERTIFICATE OF CORRECTION

PATENT NO. : 6,709,650 B1
DATED : March 23, 2004
INVENTOR(S) : Andrew D. Sutton et al.

It is certified that error appears in the above-identified patent and that said Letters Patent is hereby corrected as shown below:

Title page,
Item [73], Assignee, delete "Elam" and insert -- Elan --

Signed and Sealed this

Fourteenth Day of December, 2004

JON W. DUDAS
*Director of the United States Patent and Trademark Office*